United States Patent [19]

Baker, Jr.

[11] Patent Number: 4,856,524
[45] Date of Patent: Aug. 15, 1989

[54] A-V RESPONSIVE RATE ADAPTIVE PACEMAKER

[75] Inventor: Ross G. Baker, Jr., Houston, Tex.

[73] Assignee: Intermedics, Inc., Angleton, Tex.

[21] Appl. No.: 237,429

[22] Filed: Aug. 29, 1988

[51] Int. Cl.⁴ ............................................. A61N 1/36
[52] U.S. Cl. ............................................. 128/419 PG
[58] Field of Search ............................. 128/419 PG

[56] References Cited

U.S. PATENT DOCUMENTS

| | | | |
|---|---|---|---|
| 4,228,803 | 10/1980 | Rickards | 128/418 PG |
| 4,298,007 | 11/1987 | Wright et al. | 128/419 PG |
| 4,312,355 | 1/1982 | Funke | 128/419 PG |
| 4,313,442 | 2/1982 | Knudson et al. | 128/419 PG |
| 4,397,316 | 8/1983 | Barthel | 128/419 PG |
| 4,421,116 | 12/1983 | Markowitz | 128/419 PG |

Primary Examiner—Francis Jaworski
Assistant Examiner—Scott Getzow
Attorney, Agent, or Firm—John R. Merkling

[57] ABSTRACT

A microprocessor controlled A-V responsive rate adaptive DDD cardiac pacemaker is disclosed. The pacemaker includes atrial and ventricular sense amplifiers for detecting P-waves and Q-waves respectively, atrial and ventricular stimulus pulse generators, and A-V interval timer times the interval between a P-wave and subsequent Q-wave. The timed interval is used by a pacing interval calculation algorithm to calculate an A-A pacing interval based on one of two linear functions depending upon whether atrial activity is spontaneous or induced. The pacing interval timer times the pacing interval. If no atrial activity is detected, the atrial stimulus pulse generator paces the atrium. The A-V interval timer also times a maximum A-V interval. If no ventricular activity is sensed in the interval, the ventricular stimulus pulse generator paces the ventricle.

18 Claims, 4 Drawing Sheets

A-V RESPONSIVE RATE ADAPTIVE PACEMAKER

BACKGROUND OF THE INVENTION

1. Field of the Invention

This invention relates to cardiac pacemakers in general and more specifically to physiologically responsive rate adaptive pacemakers. In particular, the invention is directed to a rate adaptive pacemaker responsive to variations in the cardiac A-V interval.

2. Description of Related Art

Cardiac pacemakers that provide pacing stimuli to the heart at a predetermined rate are well known in the art. Such pacemakers have taken a variety of forms including fixed rate, demand, and atrial or ventricular synchronous pacers.

Such pacemakers, while in many cases providing sufficient cardiac stimulation to sustain life, are incapable of responding to the increased cardiac demand that accompanies physical exertion. As a result, patients wearing such pacemakers have been severely limited with respect to the physical activities they may engage in.

In the past, a variety of rate adaptive pacemakers have been proposed to address this problem. Of particular interest in the present case are those that are intended to respond to various physiological parameters such as the oxygen content of the blood (U.S. Pat. No. 4,399,820 to Wirtzfield), blood pressure (U.S. Pat. No. 3,828,371 to Purdy; U.S. Pat. No. 3,638,656 to Grandjean), respiratory volume (U.S. Pat. No. 3,593,718 to Krasner), and blood pH (U.S. Pat. No. 4,009,721 to Alcidi). While such physiologically responsive rate adaptive systems for the most part comprise an improvement over the known fixed rate pacemakers, at least insofar as adaptability is concerned, they also generally exhibit a number of deficiencies.

For example, the foregoing known physiologically responsive rate adaptive systems require the use of physiological sensors in addition to the pacemaker unit. The requirement of an additional sensor increases both the expense and the risk of component failure in such systems. Moreover, it has been found difficult in many cases to design sensors that can accurately measure the parameters of interest and that are sufficiently reliable to be suitable for long term implantation. It has also been found that some of the proposed physiological parameters may vary in response to artificial stimuli such as certain medications, as well as to naturally occurring stimuli, thus presenting the risk that inappropriate and undesired variations in the pacing rate may occasionally occur.

Studies have shown that another type of physiological parameter, namely the cardiac Q-T interval, also varies with physical exertion and that this variation can be detected and used to adapt the pacing rate accordingly. See, for example, the following publications: Richards, Akhras, and Baron, *Effects of Heart Rate on QT Interval*, Proceedings of the VI World Symposium on Cardiac Pacing 2:7 (Meere ed. 1979); Rickards and Norman, *Relationship Between QT Interval and Heart Rate: New Design of Physiologically Adaptive Pacemaker*, British Heart Journal 45:56–61 (1981); Donaldson, Fox, and Rickards, *Initial Experience With A Physiological, Rate Responsive Pacemaker*, British Medical Journal 286:667–671 (February, 1983). U.S. Pat. No. 4,228,803 to Rickards discloses a rate adaptive pacemaker based on the above concept that is responsive to the interval between the delivery of a pacing stimulus and the T-wave evoked thereby, hereafter referred to as the S-T interval. In the Rickard's '803 pacemaker, a pacing stimulus generator activates a T-wave detector and a S-T interval timer when a pacing stimulus is generated. The S-T interval timer times the interval between the delivery of the pacing stimulus and the detection of the evoked T-wave by a T-wave detector. The timed interval is compared with the previously timed S-T interval and the difference is used to modify the pacer escape interval.

The use of the Q-T or S-T interval as the indicator of increased cardiac demand for controlling pacing rate has advantages over the foregoing proposed physiologically responsive, rate adaptive systems. First, a pacemaker utilizing the Q-T or S-T interval as the pacing rate control parameter does not require an additional sensor external to the pacemaker unit. Thus, both cost and risk of component failure are reduced. Second, the foregoing studies have found that the Q-T interval varies primarily with the increased circulation of catecholamines in the blood stream that results directly from physical exertion and that the Q-T interval is more insensitive to variations in heart rate due to other stimuli such as medications than some other proposed parameters.

Rate adaptive pacemakers responsive to the Q-T and S-T intervals also possess several inherent disadvantages, however. As the foregoing studies have found, the T-wave is often difficult to detect due to its relatively small magnitude (typically about 2 mv) and typically extended profile. In addition, the shape of the T-wave tends to vary with postural changes making accurate detection thereof even more difficult. Further, the studies have shown the Q-T interval may also tend to decrease somewhat with increases in heart rate caused by stimuli other than physical exertion. Therefore, there is a risk that a pacemaker that is responsive to the Q-T interval may induce tachycardia under certain conditions.

The present invention overcomes the inherent disadvantages of the known Q-T and S-T responsive pacemakers while providing rate adaptive pacing completely responsive to the physiology of the heart. The improvements of the invention are the result of the discovery that the A-V interval, i.e. the interval between the depolarization of the atrium and the depolarization of the ventricle, also varies directly with increased catecholamine circulation indicative of increased cardiac demand due to physical exertion. Use of the A-V interval as the pacing rate control parameter obviates the need to detect the T-wave. Instead, the P-wave which accompanies atrial depolarization and the Q-wave which accompanies the subsequent ventricular depolarization are detected. Both waves typically are much more sharply defined than the T-wave. Thus, they are typically more accurately detected.

In addition, the A-V interval is a direct function of the conduction time through the A-V node. The A-V node exhibits a natural fatigue property characterized by increased conduction time in response to increased heart rate unaccompanied by increased catecholamine circulation. Therefore, the risk of pacemaker induced tachycardia present in Q-T responsive pacemakers is eliminated. In fact, a pacemaker embodying this invention and utilizing reduction in A-V interval as the pacing rate control parameter naturally tends to oppose increases in pacing rate unless accompanied by increased physical exertion.

In view of the foregoing, it is an object of the invention to provide an improved rate adaptive pacemaker that is responsive to the physiology of the heart and that does not require additional sensors to provide rate responsiveness.

It is another object of the invention to provide a pacemaker having additional features not found in the foregoing rate adaptive pacemakers including: (1) separate rate response functions for spontaneously occurring cardiac activity and for induced cardiac activity; (2) gradual rate response similar to that of a normally functioning human heart; and (3) a built-in bias toward spontaneous rather than paced cardiac activity.

SUMMARY OF THE INVENTION

The foregoing objects and attendant advantages are achieved by providing a cardiac pacemaker that determines the A-V interval and applies cardiac stimuli to the heart at a rate related to the determined A-V interval. According to one aspect, the pacemaker applies cardiac stimulus pulses only if selected cardiac activity is not detected during a target pacing interval related to the A-V interval. According to another aspect, the pacing rate or target interval is calculated according to a first function when selected cardiac activity is sensed and according to a second function when cardiac activity is not detected and is induced. According to still another aspect, the target pacing interval is periodically incremented to provide additional time for spontaneous cardiac activity to occur. According to a further aspect, the rate at which the pacing rate or target interval changes with changes in the A-V interval is limited.

BRIEF DESCRIPTION OF THE DRAWINGS

The invention will best be understood by reference to the detailed description of a presently preferred embodiment thereof taken in conjunction with the accompanying drawings, in which.

DETAILED DESCRIPTION OF THE PRESENTLY PREFERRED EMBODIMENTS

Figure 1:
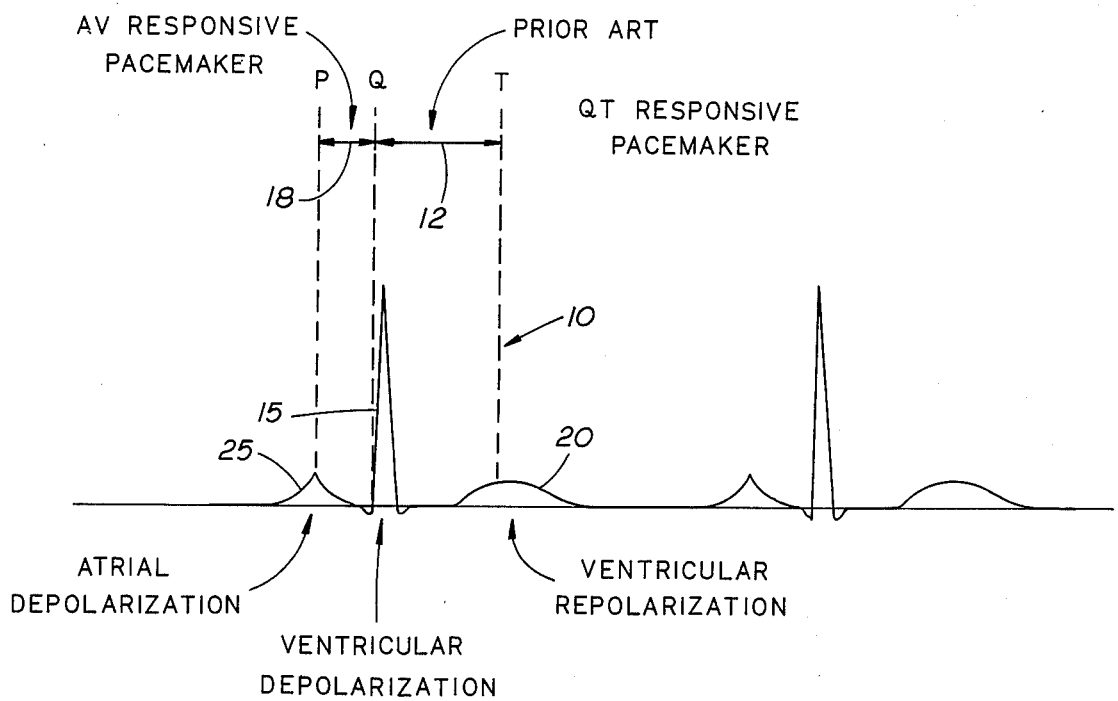
FIG. 1 is a cardiac electrical waveform illustrating the various signals and time intervals utilized in the prior art Q-T responsive pacemakers and an A-V responsive pacemaker embodying the invention.

With reference to the drawings, FIG. 1 illustrates an electrocardiogram 10 which shows the cardiac signals and time intervals utilized as rate control parameters by prior art Q-T pacemakers and by the A-V responsive pacemaker of the invention. The prior art Q-T pacemakers are designed to respond to the Q-T interval 12, i.e., the interval between the depolarization and subsequent repolarization of the ventricle. The A-V responsive pacemaker of the invention responds to the A-V interval 18, i.e. the interval between depolarization of the atrium and the subsequent depolarization of the corresponding ventricle. The A-V responsive pacemaker detects the onset of atrial depolarization by detecting the waveform 25 that is generated thereby. It detects the subsequent ventricular depolarization by detecting the Q-wave 15 that is generated thereby. Ventricular repolarization is noted at 20. The inventor has discovered that the A-V interval, like the Q-T interval, varies with changes in catecholamine circulation due to changes in the degree of physical exertion or emotional state and is therefore advantageously utilized to provide completely rate adaptive pacing.

Figure 2:
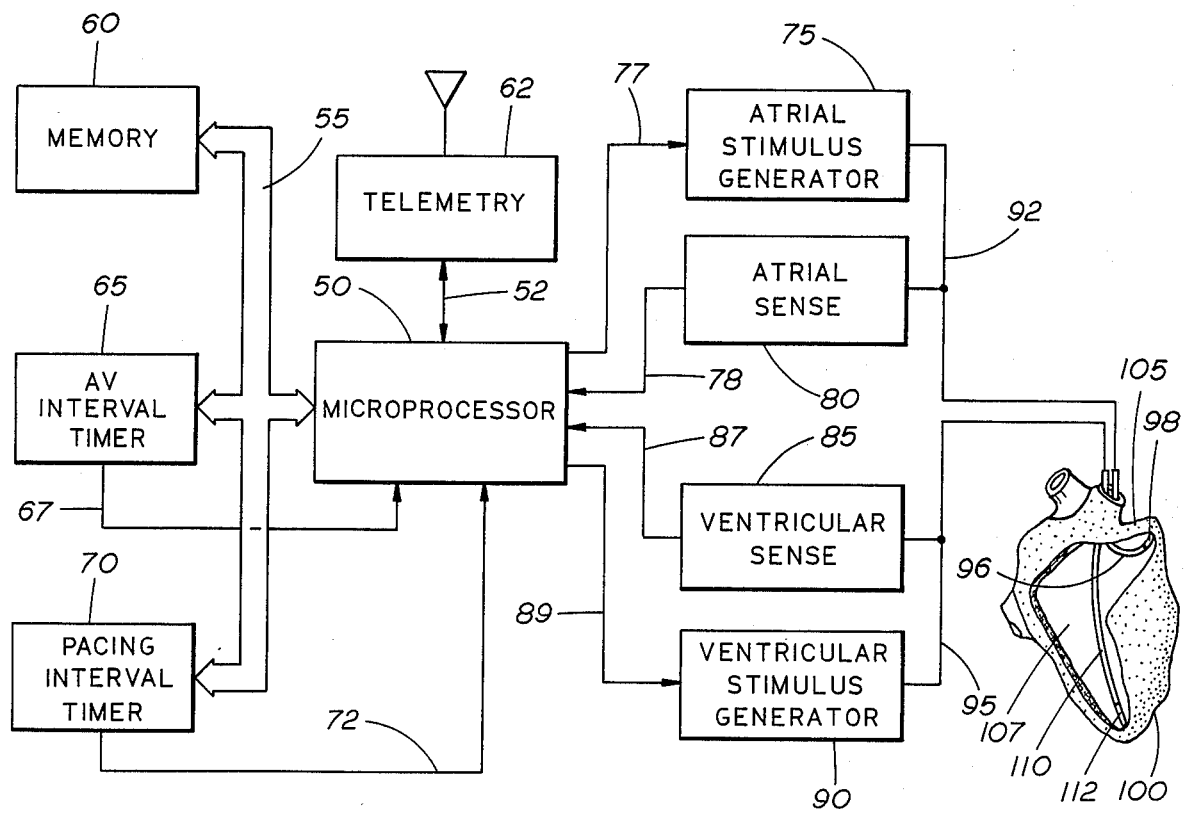
FIG. 2 is a block level diagram of a rate adaptive pacemaker of the present invention.
Figure 3:
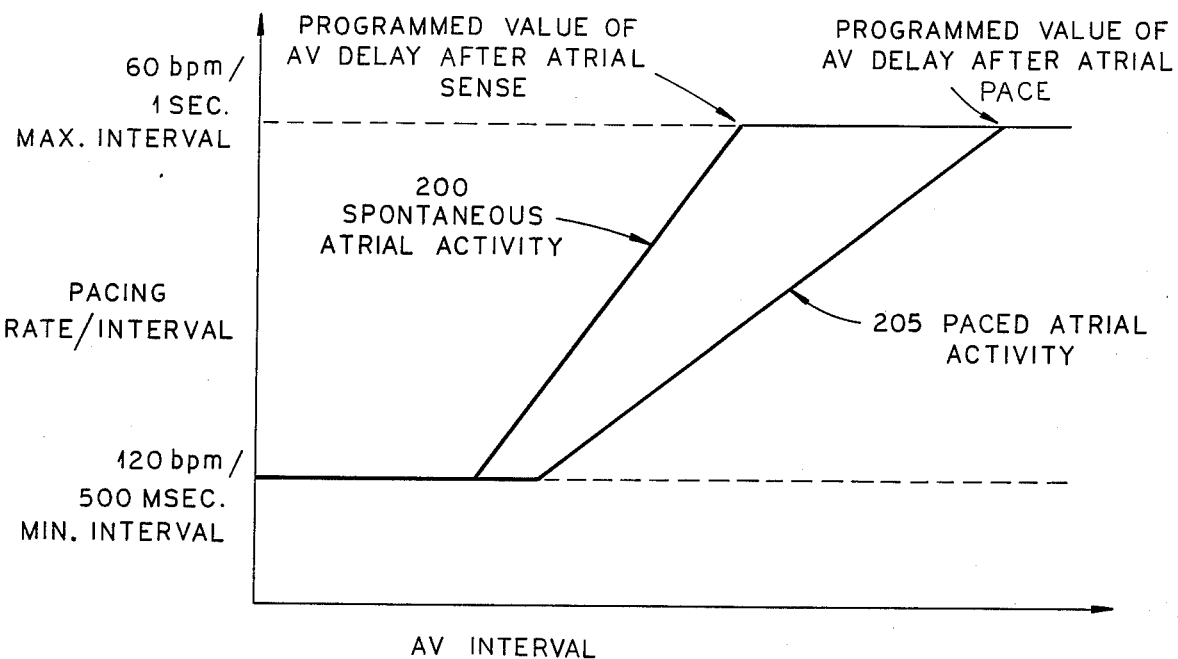
FIG. 3 is a graphical representation of the rate response functions of the subject A-V responsive pacemaker.

FIG. 2 is a block diagram illustrating a rate adaptive pacemaker of the invention. A microprocessor 50 preferably provides pacemaker control and computational facilities. It will be appreciated that other forms of circuitry, such as analog or discrete digital circuitry can be used in place of microprocessor 50. However, a microprocessor is preferred for its miniature size and its flexibility, both of which are of critical importance in the implantable systems in which it is envisioned the invention will find use. A particularly energy efficient microprocessor which is designed specifically for use herein is fully described in Gordon et al. U.S. Pat. No. 4,404,972, which is assigned to the assignee of this application and the disclosure thereof is incorporated herein by reference.

The microprocessor 50 has input/output ports connected in a conventional manner via bidirectional bus 55 to memory 60, an A-V interval timer 65, and a pacing interval timer 70. In addition, the A-V interval timer 65 and pacing interval timer 70 each has an output connected individually to a corresponding input port of the microprocessor 50 by lines 67 and 72 respectively.

Memory 60 preferably includes both ROM and RAM. The microprocessor 50 may also contain additional ROM and RAM onboard as described in the Gordon et al. '972 patent. The pacemaker operating routine is stored in ROM. The RAM stores various programmable parameters and variables which are described in detail below in conjunction with the pacemaker operation and the preferred rate control algorithm.

The A-V and pacing interval timers 65 and 70 may be external to the microprocessor 50, as illustrated, or internal thereto, as described in the Gordon et al. '972 patent. The timers 65 and 70 are suitably conventional up or down counters of the type that are initially loaded with a count value and count up to or down from the value and output a roll-over bit upon completing the programmed count. The initial count value is loaded into the timers 65 and 70 on bus 55 and the respective roll-over bits are output to the microprocessor 50 on lines 67 and 72.

The microprocessor 50 preferably also has an input/output port connected to a telemetry interface 62 by line 52. The pacemaker when implanted is thus able to receive pacing and rate control parameters from an external programmer and send data to an external receiver if desired. Many suitable telemetry systems are known to those skilled in the art. One such system and encoding arrangement is described in Calfee et al. U.S. Pat. No. 4,539,992 which is assigned to the assignee of this application. That description is incorporated herein by reference.

The microprocessor 50 has output ports connected to inputs of an atrial stimulus pulse generator 75 and a ventricular stimulus pulse generator 90 by control lines 77 and 89 respectively. The microprocessor 50 transmits pulse parameter data, such as amplitude and width, as well as enable/disable and pulse initiation codes to the generators 75 and 90 on the respective control lines.

The microprocessor 50 also has input ports connected to outputs of an atrial sense amplifier 80 and a ventricular sense amplifier 85 by lines 78 and 87 respectively. The atrial ventricular sense amplifiers 80 and 85 detect occurrences of P-waves and Q-waves respectively in a manner well known to those skilled in the art. The atrial sense amplifier 80 outputs a signal on line 78 to the microprocessor 50 when it detects a P-wave. This signal is latched to the microprocessor 50 input port by a conventional latch (not shown). The ventricular sense amplifier 85 outputs a signal on line 87 to the microprocessor 50 when it detects a Q-wave. This signal is also latched to the microprocessor 50 input port by a conventional latch (not shown).

Many suitable atrial and ventricular sense amplifiers and stimulus pulse generators are known to those skilled in the art. These elements are conventional and further detailed description thereof is not required for a complete understanding of the invention.

The input of the atrial sense amplifier 80 and the output of the atrial stimulus pulse generator 75 are connected to a first conductor 92, which is inserted in a first conventional lead 96. Lead 96 is inserted into the heart 100 intravenously or in any other suitable manner. The lead 96 has an electrically conductive pacing/sensing tip 98 at its distal end which is electrically connected to the conductor 92. The pacing/sensing tip 98 is preferably lodged in the right atrial appendage 105.

The input of the ventricular sense amplifier 85 and the output of the ventricular stimulus pulse generator 90 are connected to a second conductor 95. The second conductor 95 is inserted in a second conventional lead 110 which is inserted intravenously or otherwise in the right ventricle 107 of the heart 100. The second lead 110 has an electrically conductive pacing/sensing tip 112 at its distal end. The pacing/sensing tip 112 is electrically connected to the conductor 95. The pacing/sensing tip 112 is preferably lodged in the wall of the right ventricle.

The conductors 92 and 95 conduct the stimulus pulses generated by the atrial and ventricular stimulus pulse generators 75 and 90 respectively to the pacing/sensing tips 98 and 112. The pacing/sensing tips 98 and 112 and corresponding conductors 92 and 95 also conduct sensed cardiac electrical signals in the right atrial appendage and right ventricle similar to that shown in FIG. 1 to the atrial and ventricular sense amplifiers 80 and 85 respectively.

The A-V responsive rate adaptive features of the invention will now be described with reference to FIGS. 2-5.

Initially, a programmer or physician stores the desired pacemaker operating program into the RAM portion of the memory 60. Many different pacing modes are known to those skilled in the art including, for example, VVI, DVI, VDD, and DDD, each defining different logical pacing and sensing sequences in one or both chambers. None of the known pacing modes is inherently rate adaptive. The preferred pacemaker illustrated in FIG. 2 is preferably operated in the DDD mode.

Figure 5A:
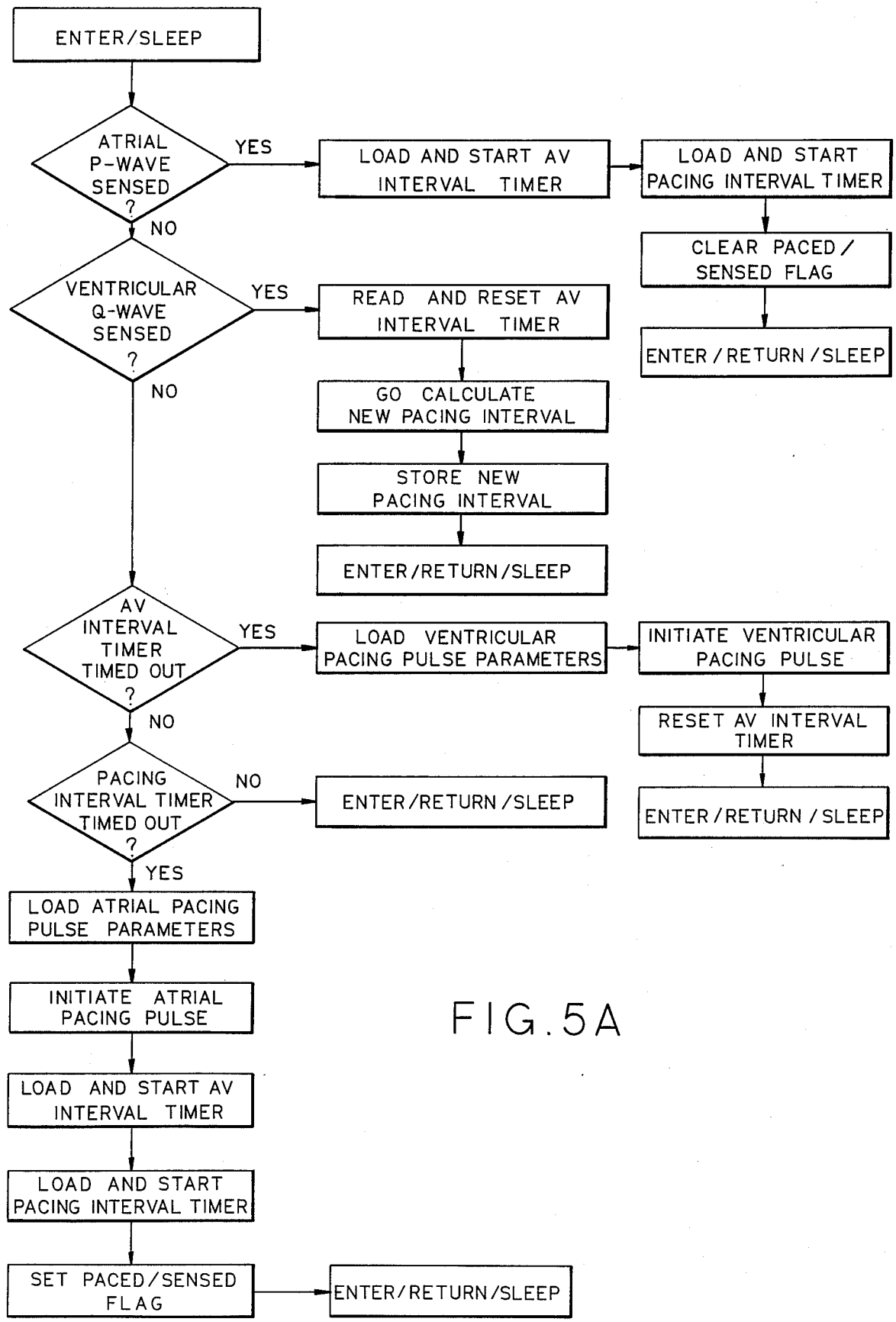
FIG. 5a. is a flow chart illustrating the operation of the subject A-V responsive pacemakers.
Figure 5B:
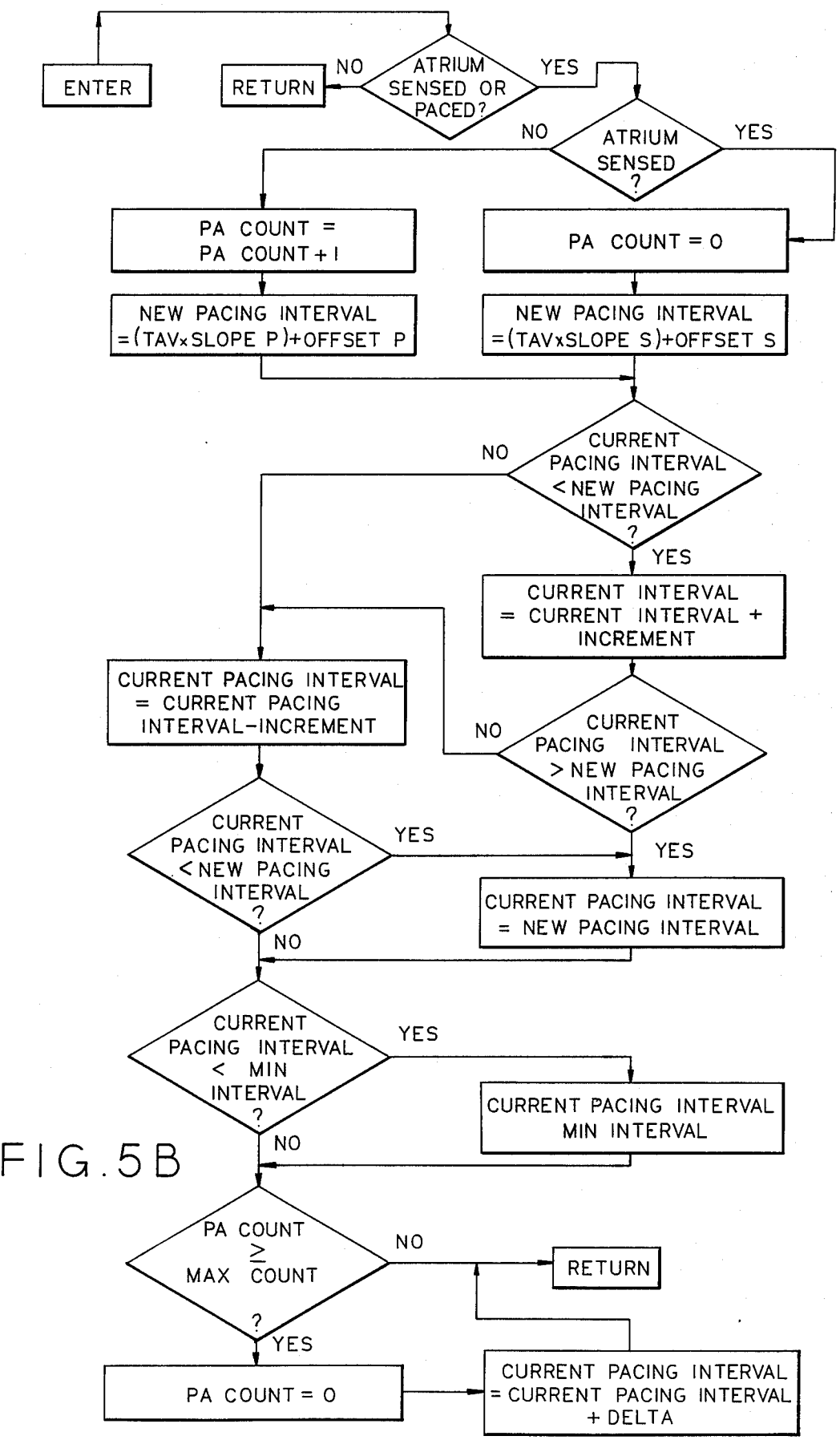
FIG. 5b. is a flow chart illustrating the operation of an A-V responsive pacing interval calculation algorithm of the subject pacemaker.

According to the invention, the operating program of the preferred DDD pacemaker of FIG. 2 comprises or includes the rate control and calculation algorithms illustrated in flow chart form in FIGS. 5a and 5b. When the rate control algorithm is entered, possibly from a sleep state in the case of the preferred microprocessor described in the Gordon et al. '972 patent, it tests the signal on the microprocessor 50 input port connected to the atrial sense amplifier 80 to determine if a P-wave has been detected. If a P-wave has been detected, the A-V interval timer 65 is loaded with a maximum A-V interval value and enabled to start counting. A typical maximum A-V interval value is approximately 200 milliseconds. At a typical timer clock rate of approximately 1.5 KHz, this corresponds to an initial count value of approximately 300. The pacing interval timer 70 is loaded with the current pacing interval count value, which is calculated similarly, and is enabled to start counting. Next, the algorithm clears a paced/sensed flag to indicate that spontaneous atrial activity was sensed. The algorithm may then loop back to the initial entry point, return to a main program, or cause the microprocessor to enter a sleep state as described in the Gordon et al. '972 patent.

The pacing interval and maximum A-V interval count parameters are preferably initially input via the telemetry interface 62 and stored in memory 60 by the microprocessor 50. Thereafter, the pacing interval count is automatically recalculated as a function of the measured A-V interval as described below. The maximum A-V interval count is not recalculated and is only changed by entering a new value through the telemetry interface 62.

If a P-wave was not detected, the microprocessor 50 input port connected to the ventricular sense amplifier 85 is tested to determine if a Q-wave has been detected. If a Q-wave has been detected, the current count value of the A-V interval timer 65 is read by the microprocessor 50 via bus 55 and the timer 65 is reset. The difference between the initial A-V interval timer count value and the value read indicates the time interval between the detection of the previous P-wave and the detection of the corresponding Q-wave. Thus, for example, given a typical clock rate of approximately 1.5 KHz, a count difference of 180 corresponds to a measured A-V interval of approximately 120 milliseconds.

The control algorithm next passes control to a pacing interval calculation algorithm which is illustrated in flow chart form in FIG. 5b and described in detail below. The preferred pacing interval calculation algorithm uses the measured A-V interval to calculate a new pacing interval as described below. In the preferred embodiment, the pacing interval is calculated as an A—A interval. Thus, the value of the pacing interval sets the time after the occurrence of a P-wave in which another P-wave must occur spontaneously to inhibit atrial pacing. It is understood, however, that the pacing interval can also be calculated as an A-V or even a V-A interval as desired for different applications.

Upon return from the pacing interval calculation algorithm the control algorithm stores the new pacing interval value in memory 60 and loops to the initial entry point, returns to a main program, or causes the microprocessor 50 to enter a sleep state.

If no P-wave or Q-wave has been detected, the control algorithm tests the microprocessor 50 input port connected to the output of the A-V interval timer 65 to determine whether the maximum A-V interval has expired. If the A-V interval timer 65 has timed out without a Q-wave being detected, the control algorithm causes pacing of the ventricle by loading the desired pulse parameters into the ventricular stimulus pulse generator 90 via line 89 and sending the appropriate command to generate a pulse. The control algorithm then resets the A-V interval timer 65 so that it does not cause ventricular pacing the next time the control algorithm is entered. The control algorithm then loops back to the entry point, returns to a main program, or causes the microprocessor 50 to enter a sleep state.

If no P-wave or Q-wave has been detected, and the A-V interval timer 65 has not timed out, the control algorithm tests the microprocessor 50 input port connected to the output of the pacing interval timer 70 to determine whether the previously loaded pacing interval has expired. If the pacing interval timer 70 has timed out without a P-wave being detected, the control routine proceeds to initiate pacing of the atrium by loading the desired pulse parameters into the atrial stimulus pulse generator 75 via line 77 and sending the appropriate command to initiate a pulse therefrom.

The control algorithm then reloads the A-V interval timer 65 with the maximum A-V interval count value (which may be different from the A-V interval loaded after a sensed P-wave) and enables it to start counting. The control algorithm also loads the pacing interval timer with the current pacing interval value and enables it to count. It then sets a paced/sensed flag to indicate that the atrium has been paced and loops back to the entry point, returns to a main program, or enters a sleep state.

If no P-wave or Q-wave was detected and neither the A-V interval timer 65 nor the pacing interval timer 70 has timed out, the routine loops back to the entry point, returns to a calling program, or puts the microprocessor to sleep without taking further action.

The preferred pacing interval calculation algorithm is illustrated in flow chart form in FIG. 5b. The algorithm first determines that the atrium was either paced or sensed during the previous cardiac cycle. If neither event occurred (for example, after a premature ventricular contraction) no new rate is calculated and it immediately returns to the calling program.

If the atrium was paced or sensed, the algorithm tests the paced/sensed flag to determine which event occurred. If the flag is set, indicating that the atrium was paced, the algorithm increments a paced count variable PA COUNT and calculates the new pacing interval as a first linear function of the measured A-V interval. If, however, the atrium was sensed, the algorithm resets the PA COUNT variable to zero and calculates the new pacing interval value as a second linear function of the measured A-V interval. Both rate functions are illustrated graphically in FIG. 3.

Function 200 relates the measured A-V interval to the desired pacing interval when a spontaneously occurring P-wave was sensed during the previous cardiac cycle. Function 205 relates the measured A-V interval to the desired pacing interval when a P-wave was induced by an atrial stimulus pulse in the previous cycle. The different slopes and offsets of the two rate functions 200 and 205 are selected to compensate the calculated pacing interval for certain differences in spontaneous and stimulated cardiac response in order to obtain a pacing interval response that is consistent regardless of whether the heart is paced or beating spontaneously.

For example, when an atrial pacing pulse is delivered, the onset of the induced P-wave is known exactly as the time of the pacing pulse. However, when a naturally occurring P-wave is sensed, there is a delay between the onset of the wave and the time when the wave exceeds the detection threshold of the atrial sense amplifier 80. This time difference can be compensated for by adjusting the offset of the function 200.

Also, the naturally occurring A-V interval is a function both of the conduction time through the A-V node and the conduction times between the sinus node and the A-V node, and the A-V node and the ventricular pacing/sensing tip 112. However, when the atrium is paced, the pacing pulse is not applied at the sinus node, but typically in the atrial appendage 105 illustrated in FIG. 2. There typically is a difference between the conduction time from the sinus node to the A-V node and from the atrial appendage to the AV node. This difference can likewise be compensated for by adjusting the relative slope and offset of the rate functions 200 and 205.

Persons skilled in the art will recognize that other functions, including certain non-linear functions can also be used to relate the pacing interval to the measured A-V delay. However, a linear function is preferred for ease of calculation.

After calculating the new pacing interval, the algorithm tests whether the current pacing interval is less than the new interval. If it is, the algorithm increments the current interval by a preselected value. If the incremented interval exceeds the calculated interval, it is set equal to the calculated interval. Likewise, if the current interval is greater than the new calculated interval, it is decremented by a preselected value. If the decremented interval is less than the calculated interval, it is set equal to the calculated interval. In this way, the preferred algorithm limits the rate of change of the pacing interval. Thus, the rapid increase and decrease of catecholamine levels in the bloodstream with the onset and stopping of physical exertion respectively do not result in abrupt rate variations. Rather smooth, gradual rate response similar to that of a normally functioning heart is obtained.

Next, the pacing interval calculation algorithm tests the PA COUNT variable to determine if it equals or exceeds a predetermined value MAX-COUNT. If it does not, the algorithm returns to the control algorithm. If, however, PA-COUNT equals or exceeds the value of MAX-COUNT, thus indicating that the atrium has been paced for at least the last consecutive MAX-COUNT cardiac cycles, the algorithm resets PA-COUNT and increases the current pacing interval by a preselected value DELTA. This periodic one-cycle interval adjustment allows the atrium extra time in which to spontaneously depolarize. Thus, if the atrium is capable of sustaining spontaneous cardiac activity a least part of the time but naturally occurring P-waves have not been detected due to fusion with pacemaker induced P-wave response, the additional interval provides an opportunity for the atrium to revert to spontaneous operation.

Each of the pacing interval calculation algorithm parameters MAX-AV-INTERVAL, MIN-INTERVAL, SLOPE-P, SLOPE-S, OFFSET-P, OFFSET-S, MAX-COUNT, INCREMENT, and DELTA is programmable. That is, each of the values is selected by a physician or programmer and is input to the pacemaker via the telemetry interface 62. The parameter values are then stored in memory 60 for use by the pacing interval calculation algorithm. Typical values for the parameters are as follows:

| | |
|---|---|
| MAX-AV-INTERVAL after an atrial pace | 200 milliseconds |
| MAX-AV-INTERVAL after an atrial sense | 160 milliseconds |
| MIN-INTERVAL | 500 milliseconds |
| SLOPE-P | 15 millisecond per msec |
| SLOPE-S | 15 millisecond per msec |
| OFFSET-P | 2000 milliseconds |
| OFFSET-S | 1400 milliseconds |
| MAX-COUNT | 20 milliseconds |
| INCREMENT | 10 milliseconds |
| DELTA | 100 milliseconds |

Figure 4:
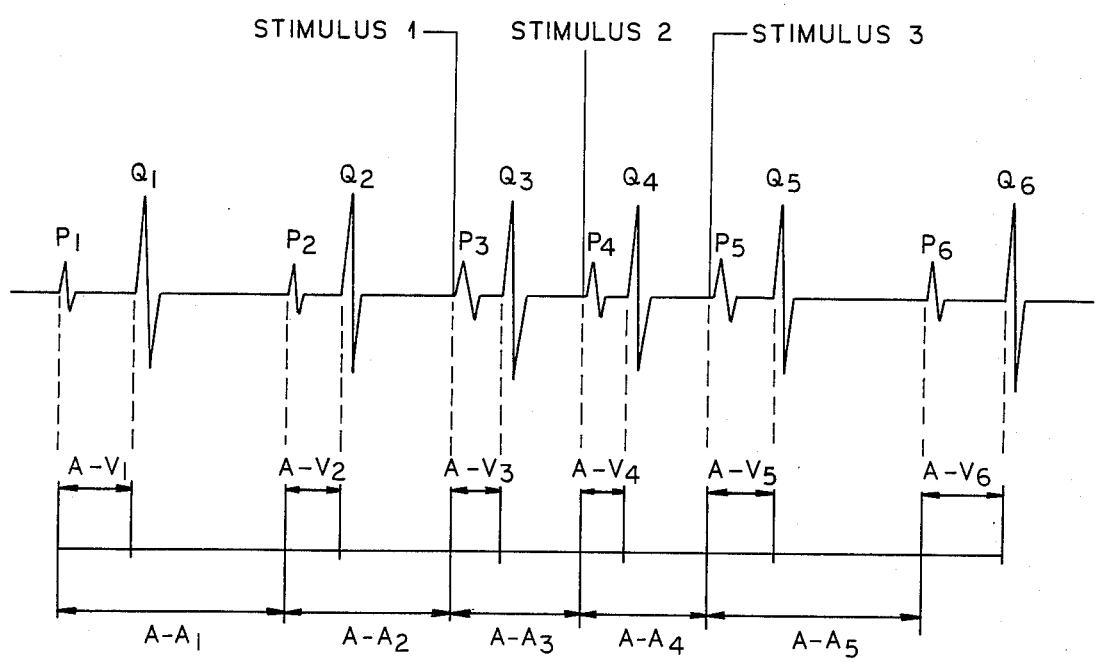
FIG. 4 is a diagrammatic representation of a cardiac electrical waveform illustrating the rate responsiveness of the subject pacemaker with respect to changes in the A-V interval.

FIG. 4 illustrates graphically the relationship between the measured A-V interval and the calculated pacing interval. In the first cardiac cycle, an A-V interval A-V$_1$ is measured between the onset of P-wave P$_1$, and Q-wave Q$_1$. In the second cardiac cycle, P-wave P$_2$ is detected before the end of the pacing interval calculated as a linear function of A-V$_1$ by the pacing interval calculation algorithm. Thus, the interval A—A$_1$ represents a spontaneous atrial to atrial interval.

In the second cardiac cycle, the measured A-V interval A-V$_2$ between P-wave P$_2$ and Q-wave$_2$ decreases in comparison to the preceding interval A-V$_1$. The reduction in A-V interval indicates the presence of increased physical exertion requiring increased cardiac output as described previously. The pacing interval calculation algorithm calculates a new pacing interval related to A-V$_2$. In this cycle, no P-wave is detected before the calculated pacing interval expires. As a result a stimulus pulse is delivered to the atrium and induces P-wave P$_3$. Thus, the interval A—A$_2$ corresponds to the calculated pacing interval.

As the measured A-V intervals A-V$_3$ and A-V$_4$ continue to decrease in subsequent cardiac cycles 3 and 4, the calculated pacing interval decreases correspondingly. In each cycle the calculated pacing interval expires before a spontaneous P-wave is detected. Thus, in both cycles a stimulus pulse is delivered to induce a P-wave and the intervals A—A$_3$ and A—A$_4$ represent paced atrial intervals.

In cardiac cycle five, the measured A-V interval A-V$_5$ increases in comparison to the immediately preceding intervals, thus indicating that the physical exertion has lessened or halted. A spontaneously occurring P-wave P$_6$ is detected before the expiration of the calculated pacing interval and no stimulus pulse is delivered. Thus, the interval A—A$_5$ again represents a spontaneous atrial to atrial interval.

The sixth cardiac cycle is only partially illustrated. However, it is seen that the measured A-V interval A-V$_6$ again increases in time. Accordingly, it will be appreciated from the foregoing that the calculated pacing interval will likewise increase to adjust the atrial rate downwardly from the increased rate present during physical exertion.

From the foregoing description it should be appreciated that the pacemaker according to the invention provides completely rate adaptive DDD pacing in the event of intermittent or complete sinus node failure when the A-V node is unimpaired. Moreover, the pacemaker can continue to provide rate adaptive pacing in the event of intermittent A-V node failure when the sinus node is unimpaired. In the latter case, a selected A-V interval value is initially input via the telemetry interface 62 as a parameter for use by the pacing interval calculation algorithm. Thereafter, when spontaneous A-V intervals are intermittently detected, they are used by the algorithm to calculate a pacing interval in the same manner as described above. However, whenever a pacemaker-induced A-V interval is detected, the algorithm reverts back to the predetermined A-V interval parameter to calculate the pacing interval. Thus, rate adaptive pacing is provided without danger of inducing a tachycardia condition.

What have been described are various aspects of an A-V responsive rate adaptive pacemaker which constitutes a presently preferred embodiment of the invention. It is understood that the foregoing description and accompanying illustrations merely exemplify certain aspects of the invention and are in no way intended to be limiting. Various changes and modifications to the preferred embodiments will be apparent to those skilled in the art. For example, various alternative modes of pacing can be employed, parameter values can be varied, the functional relationship between the A-V and pacing intervals can be altered, and the pacing interval can be adjusted in terms of A—V or V—A interval rather than the A—A interval. Such modifications and changes as well as others that will occur to those skilled in the art can be made without departing from the spirit and scope of the invention. Accordingly, it is intended that all such changes and modifications as well as other equivalents be covered by the following claims.

I claim:

1. A cardiac pacemaker, comprising:
    means for measuring the duration of an A-V interval in a heart and providing an output indicative of said measured interval; and
    means responsive to said measuring means for applying cardiac stimuli to said heart at a rate related to said measured A-V interval duration.

2. The cardiac pacemaker defined in claim 1, wherein said means for measuring A-V interval comprises:
    first means for detecting an atrial event comprising depolarization or stimulation;
    second means for detecting ventricular depolarization; and
    timing means responsive to said first and second detecting means for timing the interval between the detecting of said atrial and said ventricular depolarization.

3. The cardiac pacemaker defined in claim 1, wherein said means for applying cardiac stimuli comprises:
    means for calculating a pacing rate related to said measured A-V interval;
    means for generating pacing stimulus pulses at said calculated rate; and
    means for delivering said pulses to the heart.

4. The cardiac pacemaker defined in claim 3, wherein said means for calculating said pacing rate comprises:
    means for calculating said pacing rate according to a first function when spontaneous atrial activity is detected and according to a second function when atrial activity is induced.

5. The cardiac pacemaker defined in claim 1, wherein said means for applying cardiac stimuli comprises:
    means for calculating an atrial pacing escape interval related to said A-V interval;
    means for generating an atrial pacing pulse when no spontaneous cardiac activity occurs during said atrial pacing escape interval; and means for delivering said pacing pulse to the heart.

6. The cardiac pacemaker defined in claim 5, further comprising:
means for periodically incrementing said escape interval temporarily to allow spontaneous cardiac activity to occur.

7. The cardiac pacemaker defined in claim 1, wherein said means for applying cardiac stimuli to the heart comprises;
means responsive to changes in said A-V interval limiting the rate of change to initially less than the desired rate at which said cardiac stimuli are applied so as to approach an optimum rate slowly thereby avoiding overshoot.

8. A cardiac pacemaker comprising:
means for measuring the duration of the A-V interval;
means for measuring an atrial pacing escape interval related to said measured A-V interval;
means for sensing selected cardiac activity during said measured atrial pacing escape interval; and
means for applying a pacing stimulus pulse to the heart if said selected cardiac activity is not detected during said measured atrial pacing escape interval.

9. The cardiac pacemaker defined in claim 8, wherein said means for measuring A-V interval comprises:
first means for detecting atrial depolarization and pacing;
second means for detecting ventricular depolarization; and
timing means responsive to said first and second means for timing the interval between the detection of said atrial and said ventricular depolarization.

10. The cardiac pacemaker defined in claim 8, wherein said means for measuring said pacing escape interval comprises:
means for calculating said escape interval according to a first function when said selected cardiac activity is sensed and according to a second function when said selected cardiac activity is not sensed.

11. The cardiac pacemaker defined in claim 8, further comprising:
means for periodically temporarily incrementing said pacing escape interval to provide additional time for said selected cardiac activity to occur.

12. The cardiac pacemaker defined in claim 8, further comprising:
means responsive to changes in said A-V interval to limit the rate at which said pacing escape interval changes so as to approach an optimum pacing rate while avoiding overshoot.

13. A cardiac pacemaker, comprising:

a sensor means for detecting cardiac atrial and ventricular activity;
control circuit means responsive to said sensor means, including first timing means for timing the A-V interval between paced or sensed atrial activity and ventricular sensed activity detected by said sensor means, means for calculating a target pacing interval related to said timed A-V interval, second timing means for timing a current pacing interval, and means for initiating pacing if selected cardiac activity is not detected by said sensor means during said target pacing interval; and
pacing stimulus generator means responsive to said control circuit means for generating and delivering pacing stimulus pulses to the heart.

14. The cardiac pacemaker defined in claim 13, wherein said means for calculating a target pacing interval comprises:
means for calculating said target pacing interval according to a first function when said sensor means detect atrial activity, and according to a second function when said sensor means does not detect said atrial activity.

15. The cardiac pacemaker defined in clam 13, wherein said means for calculating said target pacing interval further comprises:
means for periodically incrementing said target pacing interval to allow extra time for selected spontaneous cardiac activity to occur.

16. The cardiac pacemaker defined in claim 13 wherein said control circuit means further comprises:
means responsive to changes in said A-V interval for limiting the rate of change of said calculated target pacing interval so as to avoid overshooting an optimum pacing rate.

17. The cardiac pacemaker defined in claim 13 wherein said target pacing interval is related to said A-V interval by a linear function relating said timed A-V interval to said target pacing rate interval.

18. A method of pacing a heart, comprising the steps of:
(a) starting an A-V interval timer upon detecting natural or paced artrial activity;
(b) stopping said A-V interval timer upon detecting natural or paced ventricular activity;
(c) calculating a target pacing interval related to the timed A-V interval;
(d) timing said target pacing interval;
(e) detecting selected cardiac activity during said target pacing interval; and
(f) generating and delivering a pacing stimulus pulse to the heart if said selected cardiac activity is not detected during said target pacing interval.

* * * * *